(12) United States Patent
Kim et al.

(10) Patent No.: US 10,921,325 B2
(45) Date of Patent: *Feb. 16, 2021

(54) COMPOSITION FOR ANTICANCER ADJUVANT COMPRISING RIP3 EXPRESSION PROMOTER AS ACTIVE INGREDIENT, METHOD FOR SCREENING ANTICANCER ADJUVANT WHICH PROMOTES RIP3 EXPRESSION AND ENHANCES SENSITIVITY OF ANTICANCER AGENT, AND METHOD FOR MONITORING SENSITIVITY OF ANTICANCER AGENT

(71) Applicant: AJOU UNIVERSITY INDUSTRY-ACADEMIC COOPERATION FOUNDATION, Gyeonggi-do (KR)

(72) Inventors: You-Sun Kim, Gyeonggi-do (KR); Gi Bang Koo, Chungcheongnam-do (KR)

(73) Assignee: AJOU UNIVERSITY INDUSTRY-ACADEMIC COOPERATION FOUNDATION, Gyeonggi-do (KR)

(*) Notice: Subject to any disclaimer, the term of this patent is extended or adjusted under 35 U.S.C. 154(b) by 229 days.

This patent is subject to a terminal disclaimer.

(21) Appl. No.: 15/750,421

(22) PCT Filed: May 7, 2016

(86) PCT No.: PCT/KR2016/004777
§ 371 (c)(1),
(2) Date: Feb. 5, 2018

(87) PCT Pub. No.: WO2017/022932
PCT Pub. Date: Feb. 9, 2017

(65) Prior Publication Data
US 2018/0231553 A1    Aug. 16, 2018

(30) Foreign Application Priority Data
Aug. 5, 2015  (KR) ..................... 10-2015-0110694

(51) Int. Cl.
| | | |
|---|---|---|
| A61K 31/704 | (2006.01) |
| G01N 33/574 | (2006.01) |
| A61K 31/7068 | (2006.01) |
| G01N 33/50 | (2006.01) |
| A61K 31/7048 | (2006.01) |
| A61K 31/404 | (2006.01) |
| A61K 31/282 | (2006.01) |
| A61K 31/506 | (2006.01) |
| A61K 47/66 | (2017.01) |
| A61P 35/00 | (2006.01) |
| A61K 38/45 | (2006.01) |
| A61K 33/24 | (2019.01) |

(52) U.S. Cl.
CPC ......... *G01N 33/574* (2013.01); *A61K 31/282* (2013.01); *A61K 31/404* (2013.01); *A61K 31/506* (2013.01); *A61K 31/704* (2013.01); *A61K 31/7048* (2013.01); *A61K 31/7068* (2013.01); *A61K 38/45* (2013.01); *A61K 47/66* (2017.08); *A61P 35/00* (2018.01); *G01N 33/5011* (2013.01); *G01N 33/57496* (2013.01); *A61K 33/24* (2013.01); *A61K 2300/00* (2013.01)

(58) Field of Classification Search
CPC combination set(s) only.
See application file for complete search history.

(56) References Cited

U.S. PATENT DOCUMENTS

2004/0224919 A1   11/2004   Rubinfeld et al.
2010/0323034 A1   12/2010   Tanigawara et al.

FOREIGN PATENT DOCUMENTS

| KR | 10-2015-0094527 | 8/2015 |
| WO | WO 2008/104543 | 9/2008 |

OTHER PUBLICATIONS

Fu et al BMC Cancer 13:1-10, 2013, IDS filed on Mar. 16, 2018, NPL1 (Year: 2013).*
Fu, Z. et al., "The Anti-Tumor Effect of Shikonin on Osteosarcoma by Inducing RIP1 and RIP3 Dependent Necroptosis," *BMC Cancer*, 13:580, pp. 1-10, BioMed Central, United Kingdom (2013).
He, J.X. et al., "Differential Sensitivity of RIP3-proficient and Deficient Murine Fibroblasts to Camptothecin Anticancer Drugs," *Acta Pharm. Sinica*, 33:426-428, Nature Publishing Group, United Kingdom (2012).
Koo, G.B. et al., "Methylation-Dependent Loss of RIP3 Expression in Cancer Represses Programmed Necrosis in Response to Chemotherapeutics," *Cell Research*, 25:707-725, Nature Publishing Group, United Kingdom (May 8, 2015).
(Continued)

*Primary Examiner* — Lei Yao
(74) *Attorney, Agent, or Firm* — Potomac Law Group, PLLC

(57) ABSTRACT

The present invention relates to a pharmaceutical composition for an anticancer adjuvant comprising a receptor-interacting protein kinase-3 (RIP3) protein expression promotor or activator as an active ingredient. In addition, the present invention provides a method of promoting cancer cell apoptosis, characterized by co-administering an anticancer agent and a RIP3 protein expression promotor or activator to cancer cells. Also, the present invention relates to a method for screening an anticancer adjuvant which promotes RIP3 expression and enhances sensitivity of an anticancer agent, and a method for monitoring sensitivity of an anticancer agent depending on the RIP3 expression. Accordingly, in the case of a patient lacking the expression of RIP3, it is expected to be an effective treatment strategy to pre-treat a demethylating agent to induce the expression of RIP3 and then to use a conventional chemotherapeutic agent. In addition, in chemotherapy, it is anticipated that the present invention may be an effective strategy in screening an anticancer adjuvant which monitors and enhances sensitivity of an anticancer agent.

3 Claims, 11 Drawing Sheets

(56) References Cited

OTHER PUBLICATIONS

Morgan, M.J. et al., "The Serine Threonin Kinase RIP3: Lost and Found," *BMB Reports*, 48(6):303-312, The Korean Society for Biochemistry and Molecular Biology, South Korea (Jun. 30, 2015).

Lu, C. et al., "RIP3 Overexpression Sensitizes Human Breast Cancer Cells to Parthenolide in vitro via Intracellular ROS Accumulation," *Acta Pharm. Sinica*, 35:929-936, Nature Publishing Group, United Kingdom (Jun. 9, 2014).

English translation of International Search Report of PCT/KR2016/004777 dated Dec. 5, 2016, issued by Korean Intellectual Property Office.

Yoo-Sun, K., "Novel Strategy on Cancer Cell Death", No Cut News, CBS, Republic of Korea (Jun. 1, 2015).

Yoo-Sun, K., "Success on Essential Protein Expression for Killing Cancer Cells—Chemotherapy Response Enhancement by Increase in RIP3 Protein Expression in a Cancer Cell", Ministry of Science, Republic of Korea (Jun. 1, 2015).

Jeong, M., "Resensitization of Cisplatin-resistant Ovarian Cancer Cells by DNA Demethylating Agents", Master's Thesis, Korea Adv. Inst. of Sci. and Tech, Republic of Korea (2007).

* cited by examiner

COMPOSITION FOR ANTICANCER ADJUVANT COMPRISING RIP3 EXPRESSION PROMOTER AS ACTIVE INGREDIENT, METHOD FOR SCREENING ANTICANCER ADJUVANT WHICH PROMOTES RIP3 EXPRESSION AND ENHANCES SENSITIVITY OF ANTICANCER AGENT, AND METHOD FOR MONITORING SENSITIVITY OF ANTICANCER AGENT

TECHNICAL FIELD

The present invention relates to a composition for an anticancer adjuvant comprising a RIP3 expression inducing agent as an active ingredient and to an anticancer composition which is co-administered with an anticancer agent. Moreover, the present invention relates to a method of screening an anticancer adjuvant that enhances anticancer drug sensitivity by promoting RIP3 expression and to a method of monitoring sensitivity to an anticancer drug based on RIP3 expression.

BACKGROUND ART

Receptor-interacting protein kinase-3 (RIP3 or RIPK3) is an important protein in cell death, and plays its role in cell death induced by death receptor or in cell death induced by other cellular stresses. It is known that these cell death signals are induced by binding to a complex with phosphorylation- or deacetylation-dependent RIP1 and mixed lineage kinase domain-like protein (MLKL) and that any protein present in mitochondria is involved in the signals. A regulated mechanism of this signaling system is induced by cell death regulatory proteins to regulate development, as well as cell death and immune responses of lymphocytes, keratinocytes and intestinal epithelial cells. In addition, regulated necrosis plays its roles in degeneration, immunity, and many etiological processes such as infectious disease and ischemic injury.

DISCLOSURE

Technical Problem

An object of the present invention is to provide a pharmaceutical composition for an anticancer adjuvant comprising a receptor-interacting protein kinase-3 (RLP3) protein expression inducing agent or activator as an active ingredient.

Another object of the present invention is to provide a pharmaceutical composition for an anticancer adjuvant comprising a demethylating agent as an active ingredient, wherein the demethylating agent enhances anticancer drug sensitivity by inducing demethylation of methylated receptor-interacting protein kinase-3 (RIP3) protein.

Still another object of the present invention is to provide an anticancer pharmaceutical composition comprising a demethylating agent and an anticancer drug as active ingredients, wherein the demethylating agent enhances anticancer drug sensitivity by inducing demethylation of methylated receptor-interacting protein kinase-3 (RIP3) protein.

Still another object of the present invention is to provide a method of screening an anticancer adjuvant that enhances sensitivity to an anticancer drug by promoting RIP3 (receptor-interacting protein kinase-3) expression, and a method of monitoring anticancer drug sensitivity based on RIP3 expression.

Still another object of the present invention is to provide a biomarker composition for diagnosis of anticancer drug sensitivity and a kit for diagnosis of anticancer drug sensitivity, which comprise RIP3 gene or proteins expressed from the gene.

Yet another object of the present invention is to provide a method for providing information required for diagnosing prognosis of anticancer drug sensitivity, the method comprising measuring expression level of RIP3.

Technical Solution

In order to accomplish the above objects, the present invention provides a pharmaceutical composition for an anticancer adjuvant comprising a receptor-interacting protein kinase-3 (RIP3) protein expression inducing agent or activator as an active ingredient.

The present invention also provides a pharmaceutical composition for an anticancer adjuvant comprising a demethylating agent as an active ingredient, wherein the demethylating agent enhances anticancer drug sensitivity by inducing demethylation of methylated receptor-interacting protein kinase-3 (RIP3) protein.

The present invention also provides an anticancer pharmaceutical composition comprising a demethylating agent and an anticancer drug as active ingredients, wherein the demethylating agent enhances anticancer drug sensitivity by inducing demethylation of methylated receptor-interacting protein kinase-3 (RIP3) protein.

The present invention also provides a method for screening an anticancer adjuvant, comprising: bringing a test substance into contact with a cancer cell; measuring the expression or activity level of receptor-interacting protein kinase-3 (RIP3) protein in the cancer cell brought into contact with the test substance; and selecting a test substance that shows an increase in the expression or activity level of the RIP3 protein compared to a control sample.

The present invention also provides a method for monitoring anticancer drug sensitivity, comprising: measuring the expression or activity level of RIP3 protein in a cancer cell; measuring the expression or activity level of RIP3 protein in a normal tissue cell; and determining that, if the measured expression or activity level of the RIP3 protein in the cancer cell is lower than the measured expression or activity level of the RIP3 protein in the normal tissue cell, the cancer cell has anticancer drug resistance.

The present invention also provides a method for enhancing anticancer drug sensitivity, comprising: treating a cancer cell with a RIP3 protein expression inducing agent or activator, measuring the expression or activity level of the RIP3 protein in the treated cancer cell; and determining that, if the expression or activity level of the RIP3 protein after the treatment is 50-100% higher than that of a control sample before the treatment, the anticancer drug sensitivity is enhanced.

The present invention also provides a biomarker composition for diagnosis of anticancer drug sensitivity, comprising RIP3 gene or a protein expressed from the gene.

The present invention also provides a kit for diagnosis of anticancer drug sensitivity, comprising a primer for amplifying RIP3 gene or an antibody or aptamer that binds specifically to a protein expressed from the gene.

The present invention also provides a method for providing information required for diagnosing prognosis of anticancer drug sensitivity, comprising: measuring expression level of RIP3 in a cancer patient sample; measuring the expression level of RIP3 in a normal control sample; and determining that, if the measured expression level of RIP3 protein in the cancer patient sample is lower than the measured expression level of RIP3 protein in the normal control sample, the cancer patient sample has anticancer drug resistance.

The present invention also provides a method for enhancing anticancer drug sensitivity of a subject, comprising administering a demethylating agent to the subject to promote RIP3 expression.

The present invention also provides a method for treating cancer in a subject, the method comprising: administering a demethylating agent to the subject to promote RIP3 expression; and administering an anticancer drug to the subject with enhanced anticancer drug sensitivity.

The present invention also provides the use of a demethylating agent for promoting RIP3 expression to enhance anticancer drug sensitivity of a subject.

Advantageous Effects

The present invention relates to a composition for an anticancer adjuvant comprising a RIP3 expression inducing agent as an active ingredient and to an anticancer composition which is co-administered with an anticancer agent. Currently, in 90% of triple negative (ER, PR, Her2 negative) patients who pose problems in cancer therapy, low RIP3 expression can be found. A significant decrease in the expression of RIP3 in cancer tissue compared to that in normal tissue of the same patient suggests that RIP3 selectively decreases during the development and growth of tumors. Thus, in the case of patients lacking expression of RIP3, it is expected that the use of a conventional chemotherapeutic agent after the induction of RIP3 expression by pretreatment with a demethylating agent may be an effective therapeutic strategy. Moreover, the present invention relates to a method of screening an anticancer adjuvant that enhances anticancer drug sensitivity by promoting RIP3 expression and to a method of monitoring sensitivity to an anticancer drug based on RIP3 expression. Currently, in 90% of triple negative (ER, PR, Her2 negative) patients who pose problems in cancer therapy, low RIP3 expression can be found, and it can be seen that the regulation of RIP3 expression influences the anticancer drug resistance of anticancer cells. In particular, it is found that, when RIP3 expression is inhibited, cancer cells have resistance to an anticancer drug, and thus the activity of the anticancer drug is inhibited, whereas when RIP3 is expressed, the death of cancer cells increase depending on the concentration of the anticancer drug. It is expected that analysis of the expression or activity level of RIP3 may be an effective strategy for monitoring sensitivity to the anticancer drug in anticancer therapy and screening the anticancer adjuvant that enhances anticancer drug sensitivity.

MODE FOR INVENTION

Figure 1:
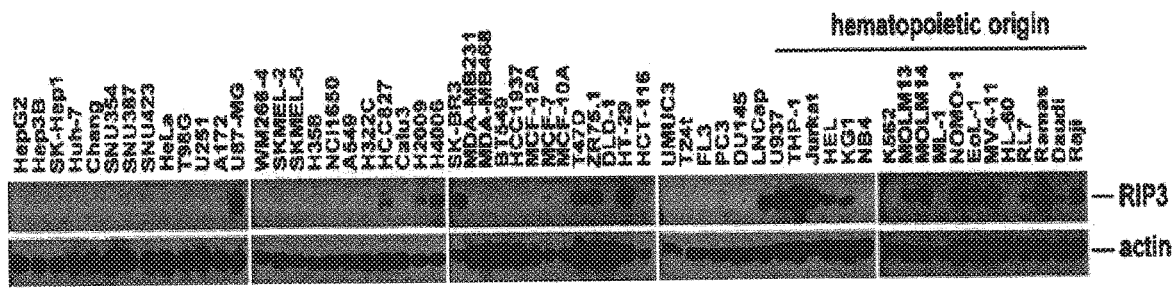
FIG. 1 shows the results of analyzing RIP3 expression in various cancer cell lines.

The present inventors have found that RIP3-dependent cell death may influence the cytotoxicity of chemotherapeutic agents. It could be found that RIP3 expression in many cancer cell lines is inhibited and this inhibition of RIP3 expression leads not only to resistance to death receptor-induced cell death, but also to resistance to chemotherapeutic agents, particularly various standard anticancer therapeutic agents such as DNA damage drugs or taxanes. It could be found that RIP3 expression is restored by the demethylating agent 5-aza-2'-deoxycytidine (5-AD) used in the present invention and that sensitivity to the chemotherapeutic agent is increased by the demethylating agent. From such results, it can be found that, in the case of patients lacking RIP3 expression, the use of a conventional chemotherapeutic agent after the induction of RIP3 expression by pretreatment with the demethylating agent may be an effective therapeutic strategy. Based on such findings, the present invention has been completed.

In addition, the present inventors have found that the regulation of RIP3 expression influences the resistance of a cancer cell line to an anticancer drug, and particularly, have found that, when RIP3 expression is inhibited, cancer cells have resistance to the anticancer drug, and thus the activity of the anticancer drug is inhibited, whereas when RIP3 is expressed, cancer cell death is increased depending on the concentration of the anticancer drug, thereby completing the present invention.

The present invention provides a pharmaceutical composition for an anticancer adjuvant comprising a receptor-interacting protein kinase-3 (RIP3) protein expression inducing agent or activator as an active ingredient.

Particularly, the RIP3 protein expression inducing agent or activator may be selected from among compounds, peptides, peptide mimetics, aptamers, antibodies and natural substances, which bind specifically to the expression regulatory region of RIP3 gene. Particularly, the composition may induce demethylation of RIP3 protein. Preferably, the RIP3 protein inducing agent or activator may be a demethylating agent.

The present invention also provides a pharmaceutical composition for an anticancer adjuvant comprising a demethylating agent as an active ingredient, wherein the demethylating agent enhances anticancer drug sensitivity by inducing demethylation of methylated receptor-interacting protein kinase-3 (RIP3) protein.

The present invention also provides an anticancer pharmaceutical composition comprising a demethylating agent and an anticancer drug as active ingredients, wherein the demethylating agent enhances anticancer drug sensitivity by inducing demethylation of methylated receptor-interacting protein kinase-3 (RIP3) protein.

Preferably, the RIP3 protein may be a protein from all eukaryotic organisms with RIP3, including mammals such as humans, cattle, goats, sheep, pigs, mice, rabbits, etc. For example, it may be human RIP3 (NCBI accession no. NP_006862.2).

As used herein, the term "peptide mimetics" refers to a peptide or non-peptide that inhibits the binding domain of RIP3 protein inducing RIP3 activity.

As used herein, the term "aptamer" refers to a single d nucleic acid (DNA, RNA or modified nucleic acid) that has a stable 3-dimensional structure and may bind to target molecules with high affinity and specificity. Since the aptamer has unique high affinity (pM level in general) and specificity for target molecules, it is comparable with monoclonal antibodies, and in particular, its potential to be used as an alternative antibody is so high that the aptamer is often called "chemical antibody".

The "antibody" that is used in the present invention may be an antibody produced by RIP3 injection or a commercially available antibody. In addition, the antibodies include a polyclonal antibody, a monoclonal antibody and a fragment capable of binding to an epitope.

The polyclonal antibody may be produced as follows. The RIP3 is injected into an animal; a blood sample is taken from the animal; and then serum containing the antibody is separated from the blood. This polyclonal antibody may be purified by any methods known to those in the art and may be produced from any animal hosts including goats, rabbits, sheep, monkeys, horses, pigs, cattle, dogs, etc. The monoclonal antibody may be produced using any technique that provides the production of antibody molecules through continuous culture of a cell line. Such techniques include, but are not limited to, hybridoma techniques, human B-cell line hybridoma techniques and EBV-hybridoma techniques.

Preferably, the demethylating agent may be, but is not limited to, 5-aza-2'-deoxycytidine (5-AD; Decitabine), 5-azacytidine (5-AZA), 1-β-arabinofuranosilcytosine (Cytarabine or ara-C), pseudoisocytidine (psi ICR), 5-fluoro-2'-deoxycytidine (FCdR), 2"-deoxy-2',2'-difluorocytidine (Gemcitabine), 5-aza-2'-deoxy-2',2'-difluorocytidine, 5-aza-2'-deoxy-2'-fluorocytidine, 1-β-D-ribofuranosyl-2(1H)-pyrimidinone (Zebularine), 2',3'-dideoxy-5-fluoro-3'-thiacytidine (Emtriva), 2'-cyclocytidine (Ancitabine), 1-β-D-arabinofuranosyl-5-azacytosine (Fazarabine or am-AC), 6-azacytidine, 5,6-dihydro-5-azacytidine (dH-aza-CR), $N^4$-pentyloxy-carbonyl-5'-deoxy-5-fluorocytidine (Capecitabine), $N^4$-oetadecyl-cytarabine, or elaidic acid cytarabine.

Preferably, the anticancer drug may be, but is not limited to, nitrogen mustard, imatinib, oxaloplatin, rituximab, erlotinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacytidine, methotrexate, uracil, cytarabine, fluorouracil, fludarabine, enocitabine, decitabine, mercaptopurine, thioguanine, cladribine, carmofiir, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunombicin, dactinomycin, pirarubicin, aclarubicin, pepromycin, temozolomide, busulfan, ifosfamide, cyclophosphamide, melphalan, altretamine, dacabazine, thiotepa, nimustine, chlorambucil, mitolactol, lomustine, or carmustine.

Preferably, the cancer may be, but is not limited to, breast cancer, cervical cancer, glioma, brain cancer, melanoma, lung cancer, bladder cancer, prostate cancer, leukemia, renal cancer, liver cancer, colorectal cancer, pancreatic cancer, gastric cancer, gallbladder cancer, ovarian cancer, lymphoma, osteosarcoma, uterine cancer, oral cancer, bronchial cancer, nasopharyngeal cancer, larynx cancer, skin cancer, blood cancer, thyroid cancer, parathyroid cancer, or ureter cancer.

The pharmaceutical composition of the present invention may contain, as active ingredients, a chemical substance, a nucleotide, an antisense, siRNA, an oligonucleotide and a natural extract. The pharmaceutical composition or combined formulation of the present invention may be prepared using pharmaceutically suitable and physiologically acceptable adjuvants in addition to the active ingredient. The adjuvants that are used in the present invention may include an excipient, a disintegrant, a sweetener, a binder, a coating agent, an expander, a lubricant, a glidant, a flavoring agent, a solubilizing agent, etc. For administration, the pharmaceutical composition of the present invention may be preferably formulated using at least one pharmaceutically acceptable carrier in addition to the active ingredient. When the composition is formulated as a liquid solution, it may contain at least one pharmaceutically acceptable carrier selected from among saline solution, sterile water, Ringer solution, buffered saline, injectable albumin solution, dextrose solution, malto-dextrin solution, glycerol, ethanol, and mixtures thereof. If necessary, other conventional additives including an antioxidant, buffer, a bacteriostatic agent, etc. may be added. In addition, a diluent, a dispersing agent, a surfactant, a binder and a lubricant may be further added to prepare injectable formulations such as aqueous solution, suspension or emulsion, etc., a pill, a capsule, a granule or a tablet.

The pharmaceutical composition of the present invention may be formulated in the form of a granule, powder, a coated tablet, a tablet, a capsule, a suppository, syrup, juice, suspension, emulsion, drop, injectable liquid, or sustained-release formulation of an active compound. The pharmaceutical composition of the present invention may be administered according to a conventional method by an intravenous, intraarterial, intraabdominal, intramuscular, intrasternal, transdermal, intranasal, inhalation, topical, rectal, oral, intraocular or intradermal route. The effective amount of the active ingredient of the pharmaceutical composition according to the present invention means an amount required for prevention or treatment of disease. Thus, the effective amount may be determined depending on various factors including the type of disease, the severity of disease, the type and content of an active ingredient and other components contained in the composition, the type of formulation, the patient's age, weight, general health conditions, sex and diet, the time of administration, the route of administration, the secretion rate of the composition, the period of treatment, and a drug that is used concurrently. For an adult, the composition may be administered once or several times a day. When being administered once or several times a day, the dose of administration may be 0.1 ng/kg-10 g/kg for a compound, 0.1 ng/g-10 g/kg for a polypeptide, a protein or an antibody, and 0.01 ng/kg-10 g/kg for an antisense nucleotide, siRNA, shRNAi or miRNA, but the scope of the present invention is not limited thereto.

The present invention also provides a method for screening an anticancer adjuvant, comprising: bringing a test substance into contact with a cancer cell; measuring the expression or activity level of receptor-interacting protein kinase-3 (RIP3) protein in the cancer cell brought into contact with the test substance; and selecting a test substance that shows an increase in the expression or activity level of the RIP3 protein compared to a control sample. Particularly, the anticancer adjuvant may enhance anticancer drug sensitivity.

Preferably, the expression or activity level of the RIP3 protein may be measured by any one selected from the group consisting of reverse transcription-polymerase chain reaction (RT-PCR), enzyme-linked immunosorbent assay (EISA), immunohistochemistry, Western blotting and flow cytometry (FACS), but the scope of the present invention is not limited thereto.

The term "test substance", as used with respect to the screening method herein, means an unknown candidate substance that is used in screening in order to examine whether it influences the expression level of a gene or whether it influences the expression or activity of a protein. The sample may include a chemical substance, a nucleotide, antisense-RNA, siRNA (small interference RNA) or a natural extract, but is not limited thereto.

The present invention also provides a method for monitoring anticancer drug sensitivity, comprising: measuring the expression or activity level of RIP3 protein in a cancer cell; measuring the expression or activity level of RIP3 protein in a normal tissue cell; and determining that, if the measured expression or activity level of the RIP3 protein in the cancer cell is lower than the measured expression or activity level of the RIP3 protein in the normal tissue cell, the cancer cell has anticancer drug resistance.

The present invention also provides a method for enhancing anticancer drug sensitivity, comprising: treating a cancer cell with a RIP3 protein expression inducing agent or activator; measuring the expression or activity level of the RIP3 protein in the treated cancer cell; and determining that, if the expression or activity level of the RIP3 protein after the treatment is 50-100% higher than that of a control sample before the treatment, the anticancer drug sensitivity is enhanced.

Preferably, the demethylating agent may be, but is not limited to, 5-aza-2'-deoxycytidine (5-AD; Decitabine), 5-azacytidine (5-AZA), 1-β-arabinofuranosilcytosine (Cytarabine or ara-C), pseudoisocytidine (psi ICR), 5-fluoro-2'-deoxycytidine (FCdR), 2'-deoxy-2',2'-difluorocytidine (Gemcitabine), 5-aza-2'-deoxy-2',2'-difluorocytidine, 5-aza-2'-deoxy-2'-fluorocytidine, 1-β-D-ribofuranosyl-2(1H)-pyrimidinone (Zebularine), 2',3'-dideoxy-5-fluoro-3'-thiacytidine (Emtriva), 2'-cyclocytidine (Ancitabine), 1-β-D-arabinofuranosyl-5-azacytosine (Fazarabine or ara-AC), 6-azacytidine, 5,6-dihydro-5-azacytidine (dH-aza-CR), $N^4$-pentyloxy-carbonyl-5'-deoxy-5-fluorocytidine (Capecitabine), $N^4$-octadecyl-cytarabine, or elaidic acid cytarabine.

Preferably, the anticancer drug may be, but is not limited to, nitrogen mustard, imatinib, oxaliplatin, rituximab, erlotinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacytidine, methotrexate, uracil, cytarabine, fluorouracil, fludarabine, enocitabine, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temozolomide, busulfan, ifosfamide, cyclophosphamide, melphalan, altretamine, dacabazine, thiotepa, nimustine, chlorambucil, mitolactol, lomustine, or carmustine.

Preferably, the cancer may be, but is not limited to, breast cancer, cereal cancer, glioma, brain cancer, melanoma, lung cancer, bladder cancer, prostate cancer, leukemia, renal cancer, liver cancer, colorectal cancer, pancreatic cancer, gastric cancer, gallbladder cancer, ovarian cancer, lymphoma, osteosarcoma, uterine cancer, oral cancer, bronchial cancer, nasopharyngeal cancer, larynx cancer, skin cancer, blood cancer, thyroid cancer, parathyroid cancer, or ureter cancer.

The present invention also provides a biomarker composition for diagnosis of anticancer drug sensitivity, comprising RIP3 gene or a protein expressed from the gene.

As used herein, the term "diagnosis" includes determining the susceptibility of a subject to a certain disease or disorder; determining whether a subject has a certain disease or disorder; determining the prognosis of a subject suffering from a certain disease or disorder; or the rametrics (for example, monitoring the condition of a subject to provide information about therapeutic efficacy).

The present invention also provides a kit for diagnosis of anticancer drug sensitivity, comprising a primer for amplifying RIP3 gene or an antibody or aptamer that binds specifically to a protein expressed from the gene.

As used herein, the term "primer" refers to a nucleic acid sequence having a short free 3'-end hydroxyl group, which is a short nucleic acid sequence that may form a base pair with a complementary template and act as a start point for template strand replication. The primer may initiate DNA synthesis in the presence of a reagent for polymerization (e.g., DNA polymerase or reverse transcriptase) and four nucleoside triphosphates in suitable buffer at a suitable temperature. PCR conditions and the lengths of the sense and antisense primers may be suitably selected according to techniques known in the art.

Furthermore, the kit of the present invention may comprise an antibody binding specifically to a marker component, a secondary antibody conjugate having a label that develops color by reaction with a substrate, a substrate solution to be reacted with the label, a wash buffer, and an enzymatic reaction stop buffer, etc. Further, the kit may be made of a plurality of packagings or compartments including the reagent components used.

The label of the secondary antibody conjugate may be preferably a conventional color development material that develops color. It may be selected from among fluoresceins such as HRP (horseradish peroxidase), alkaline phosphatase, colloid gold, RTC (poly L-lysine-fluorescein isothiocyanate), RITC (rhodamine-B-isothiocyanate), etc., and dyes.

The present invention also provides a method for providing information required for diagnosing prognosis of anticancer drug sensitivity, comprising: measuring expression level of RIP3 in a cancer patient sample; measuring the expression level of RIP3 in a normal control sample; and determining that, if the measured expression level of RIP3 protein in the cancer patient sample is lower than the measured expression level of RIP3 protein in the normal control sample, the cancer patient sample has anticancer drug resistance.

Particularly, the expression level of RIP3 may be measured by an antigen-antibody reaction. More particularly, the antigen-antibody reaction may be performed according to quantitative or qualitative immunoassay protocol known in the art. The immunoassay formats may include, but are not limited to, enzyme-linked immunosorbent assay (ELISA), radioimmunoassay (RIA), sandwich assay, Western blotting, immunoprecipitation, immunohistochemical staining, flow cytometry, fluorescence assisted cell sorting (FACS), enzyme-substrate coloring assay, and antigen-antibody aggregation.

As used herein, the term "patient sample" may be intended to include a sample including a tissue, a cell, whole blood, serum, plasma, saliva, phlegm, cerebrospinal fluid or urine, which shows a difference in the expression level of RIP3, which is a biomarker for diagnosis of anticancer drug sensitivity, from that in a normal control, but the scope of the present invention is not limited thereto.

Preferably, the anticancer drug may be, but is not limited to, nitrogen mustard, imatinib, oxaliplatin, rituximab, erlotinib, trastuzumab, gefitinib, bortezomib, sunitinib, carboplatin, sorafenib, bevacizumab, cisplatin, cetuximab, Viscum album, asparaginase, tretinoin, hydroxycarbamide, dasatinib, estramustine, gemtuzumab ozogamicin, ibritumomab tiuxetan, heptaplatin, methyl aminolevulinic acid, amsacrine, alemtuzumab, procarbazine, alprostadil, holmium nitrate chitosan, gemcitabine, doxifluridine, pemetrexed, tegafur, capecitabine, gimeracil, oteracil, azacytidine, methotrexate, uracil, cytarabine, fluorouracil, fludarabine, enocitabine, decitabine, mercaptopurine, thioguanine, cladribine, carmofur, raltitrexed, docetaxel, paclitaxel, irinotecan, belotecan, topotecan, vinorelbine, etoposide, vincristine, vinblastine, teniposide, doxorubicin, idarubicin, epirubicin, mitoxantrone, mitomycin, bleomycin, daunorubicin, dactinomycin, pirarubicin, aclarubicin, pepromycin, temozolomide, busulfan, ifosfamide, cyclophosphamide, melphalan, altretamine, dacabazine, thiotepa, nimustine, chlorambucil, mitolactol, lomustine, or carmustine.

Preferably, the cancer may be, but is not limited to, breast cancer, cervical cancer, glioma, brain cancer, melanoma, lung cancer, bladder cancer, prostate cancer, leukemia, renal cancer, liver cancer, colorectal cancer, pancreatic cancer, gastric cancer, gallbladder cancer, ovarian cancer, lymphoma, osteosarcoma, uterine cancer, oral cancer, bronchial cancer, nasopharyngeal cancer, larynx cancer, skin cancer, blood cancer, thyroid cancer, parathyroid cancer, or ureter cancer.

Hereinafter, the present invention will be described in detail with reference to examples. It is to be understood, however, that these examples are for illustrative purposes only and are not intended to limit the scope of the present invention. The examples of the present invention are provided so that this disclosure will be thorough and complete, and will fully convey the scope of the present invention to those skilled in the art.

EXPERIMENTAL EXAMPLES

The following experimental examples provide experimental examples that are applied commonly to examples of the present invention.

1. Reagents

RIP3 antibody was purchased from Abeam. Actin antibody, doxorubicin, etoposide, 5-AD and 5-AZA were purchased from Sigma-Aldrich.

2. Cell Culture

Various cancer cell lines were cultured in media provided by ATCC. DLD1, HeLa and MCF7 were cultured in DMEM media supplemented with 10% fetal bovine serum, 2 mM glutamine, 100 U/mL of penicillin and 100 g/mL of streptomycin. HCC1937, BT-549, MDA-MB231, MDA-MB468, SK-BR3, ZR75-1 and T47D were cultured in RPMI supplemented with 10% fetal bovine serum, 2 mM glutamine, 100 U/mL of penicillin and 100 ug/mL of streptomycin.

3. Normal Human Cells

Mammary epithelial cells (HMEs) were obtained from Clonetics Corp. (San Diego, Calif.). HMLEs (of normal mammary epithelial cells) were immortalized with hTERT, and also infected by retrovirus with SV40 large and small T antigens.

4. Preparation of Human Breast Cancer Tissue

Human breast cancer and control normal samples were obtained from Yonsei University College of Medicine (Seoul, Korea). In all cases, informed written consent was obtained from all participants, and this study was performed under the approval of the Institutional Review Board (IRB) of Yonsei University.

5. Lentiviral snRNA Experiments

A MISSION short-hairpin RNA (shRNA) plasmid that targets the coding region or 3' UTR of hRIP3 mRNA (NM_006871) or a non-target control sequence (NM-027088) were obtained from Sigma-Aldrich. A Lentivirus plasmid was transfected into 293T cells (System Biosciences, LV900A-1) using Lipofectamine 2000 (Invitrogen, 11668019). Pseudoviral particles were collected at 2 days after transfection of the Lentivirus plasmid and infected into various cancer cells in the presence of polybrene (10 µg/mL). At 2 days after infection, infected cells were selected with puromycin, and RIP3 knockdown was confirmed by immunoblotting. Cells without expression endogenous RIP3 were afterwards treated with 5-AD for 4 days and analyzed by immunoblotting.

6. Western Blotting (Immunoblotting)

Cells were lysed in M2 buffer. Equal amounts of cell extracts were analyzed by SDS-PAGE and immunoblotting, and visualized by enhanced chemiluminescence (ECL, Amersham).

7. Cytotoxicity Assay

Cell viability was determined using tetrazolium dye colorimetric test (MTT assay) at 570 nm.

8. Immunohistochemistry Assay

Immunohistochemistry was performed using the UltraVision LP Detection System TL-060-HD (Thermo Scientific, Bioanalytica) according to the manufactures instructions. Thin paraffin sections (4.5 μm) were deparaffinized in xylene and rehydrated in a graded series of ethanol-aqueous solutions. Antigen retrieval was done by heating the slides for 15 min in a microwave oven in 10 mM citrate buffer (pH 6.0). Endogenous peroxidase activity was blocked by incubation in 3% hydrogen peroxide in TBS for 10 min, and then the sections were incubated overnight at 4° C. in 1:300 dilutions of anti-RIP3 antibody. Chromogen was developed for 5 min with 3,3'-diaminobenzidine (TL-015-HD, Them© Scientific, Bioanalytica, Greece) solution and counterstained with Meyer's hematoxylin. Immunohistochemical staining was evaluated based on the proportion of stained cells and immunostaining intensity. H-score used in the present invention was obtained by multiplying the proportion of stained cells (i) and staining intensity graded 0 (negative), 1 (weak), 2 (moderate), or 3 (strong). H-score ranged from 0 to 300. Staining was carried out for tumor and normal tissues for each sample for the same time. Staining was interpreted by an experienced pathologist blinded to the clinical data.

9. Statistical Analysis

Data were represented by a mean±S.D. Statistical analysis was performed using ANOVA and an unpaired Student's t-test. A P-value of 0.01 or below was considered statistically significant. Statistical calculations were performed using SPSS software for Windows Version 12.0 (SPSS, Chicago, Ill., USA).

Example 1

Analysis of RIP3 Expression in Cancer Cell Lines

Various cancer cell lines (including liver cancer, cervical cancer, brain cancer, ovarian cancer, skin cancer, lung cancer, breast cancer, colorectal cancer, lymphoma, bladder cancer, prostate cancer and blood cancer cell) were lysed to extract proteins which were then subjected to Western blotting using SDS-PAGE. RIP3 expression patterns in the cancer cell lines were analyzed, and as a result, it was shown that RIP3 was not expressed in 60% or more of the cancer cell lines. It was found that RIP3 was silenced in the cancer cell lines by a specific mechanism (FIG. 1).

Example 2

Analysis of RIP3 Expression by Demethylating Agent

Figure 2:
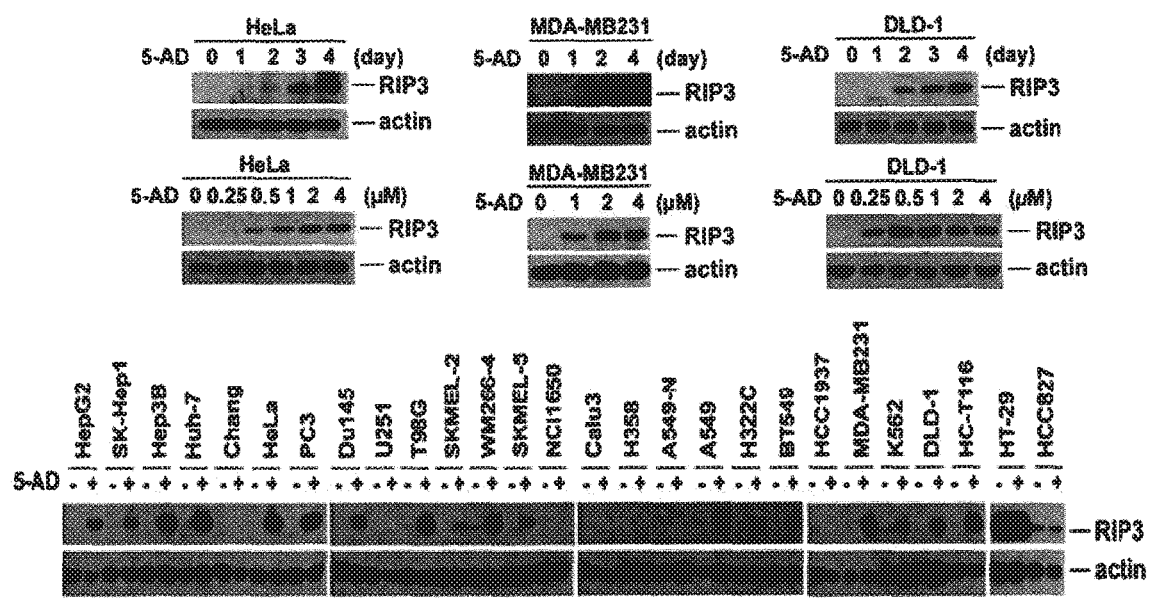
FIG. 2 shows RIP3 expression induced by 5-aza-2'-deoxycytidine (5-AD) that is a demethylating agent.

A variety of RIP3-silenced cancer cell lines (including liver cancer, cervical cancer, prostate cancer, brain cancer, ovarian cancer, skin cancer, lung cancer, breast cancer, blood cancer, colorectal cancer, and bladder cancer) were grown to a confluence of 10-20%, and then treated twice with 5-AD for 4 days, after which RIP3 expression patterns in the cell lines were analyzed by a Western blotting technique. It was shown that, when the cancer cell lines that expressed no RIP3 ware treated with a demethylating agent (5-AD, 2 uM), RIP3 expression was induced. This result suggests that RIP3 expression in the cancer cell lines as mentioned above is suppressed by methylation (FIG. 2).

Figure 3:
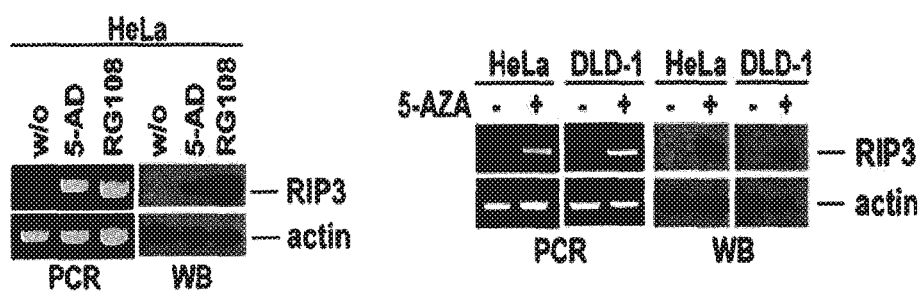
FIG. 3 shows RIP3 expression induced by the demethylating agent 5-azacytidine (5-AZA) and RG108.

In addition, it was observed at the mRNA or protein level that, when a HeLa cervical cell line and a DLD-1 colorectal cancer cell line, which expressed no RIP3, were treated with 5-AZA or RG108 belonging to a class similar to 5-AD, RIP3 expression was induced. This result demonstrates that RIP3 expression in various cancer cell lines, such as liver cancer, cervical cancer, prostate cancer, brain cancer, ovarian cancer, skin cancer, lung cancer, breast cancer, blood cancer, colorectal cancer and bladder cancer, are suppressed by methylation (FIG. 3).

Example 3

Sensitization to Cancer Cell Death by Combined Treatment with Demethylating Agent and Anticancer Drug Each of cervical cancer, breast cancer and colorectal cancer cell lines was grown to a confluence of 10-20%, and then treated twice with 5-AD or 5-AZA for 4 days to induce RIP3 expression. The same number of HeLa, MDA-MB231 and DLD-1 cancer cell lines not treated with a drug were also grown, and then treated with the same concentration of an anticancer drug. The effect of the demethylating agent on sensitization to cell death was analyzed.

Figure 4A:
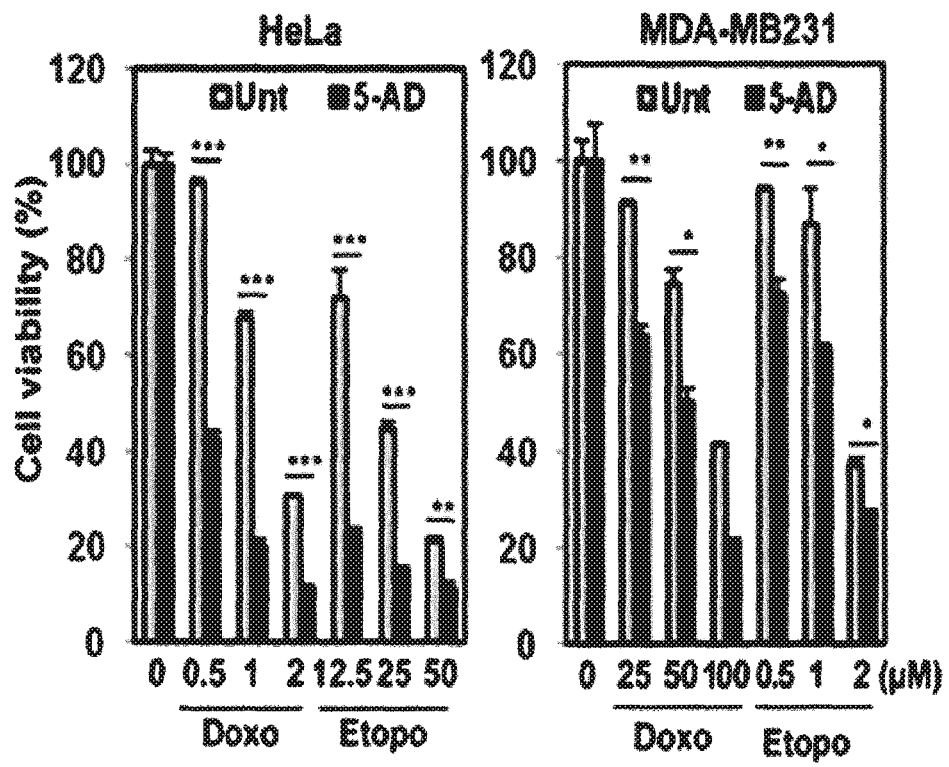
FIG. 4a shows cell viability measured when cancer cell lines were sensitized to cell by combined treatment with a demethylating agent (5-AD) and an anticancer drug.
Figure 4B:
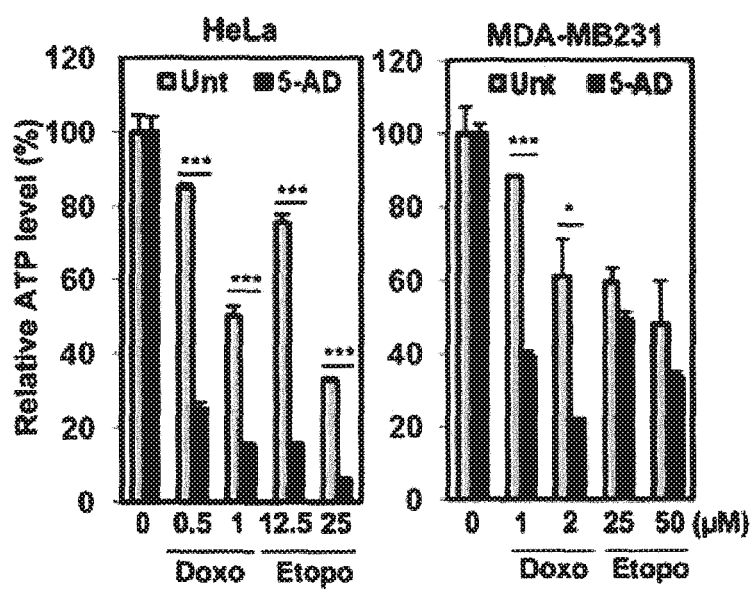
FIG. 4b shows relative ATP levels measured when cancer cell lines were sensitized to cell by combined treatment with a demethylating agent (5-AD) and an anticancer drug.
Figure 5A:
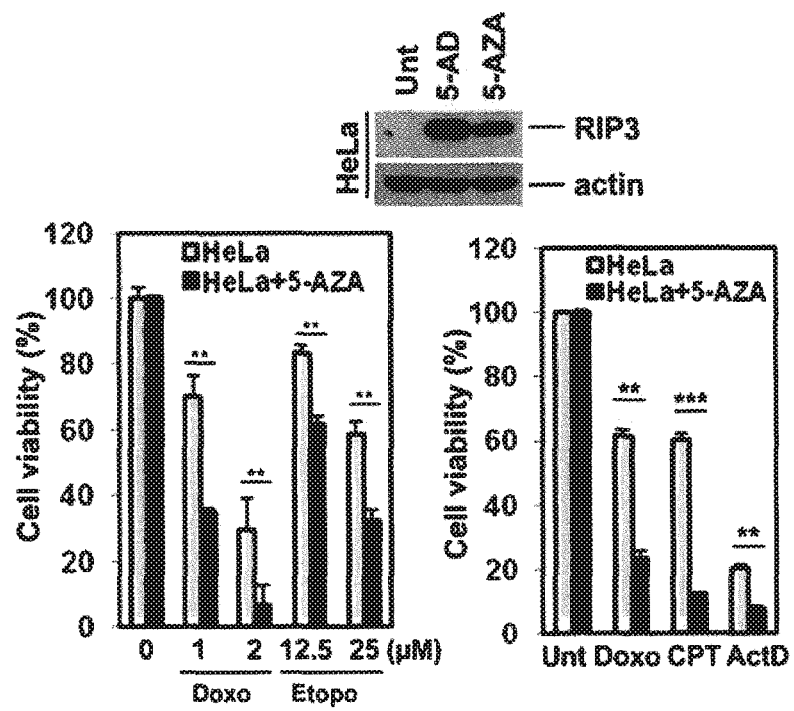
FIG. 5a shows the results of sensitizing the HeLa cancer cell line to cell death by combined treatment with a demethylating agent (5-AD or 5-AZA) and an anticancer drug.
Figure 5B:
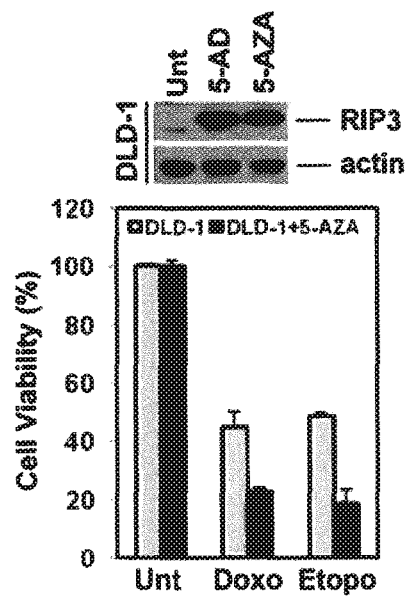
FIG. 5b shows the results of sensitizing the DLD-1 cancer cell line to cell death by combined treatment with a demethylating agent (5-AD or 5-AZA) and an anticancer drug.
Figure 6:
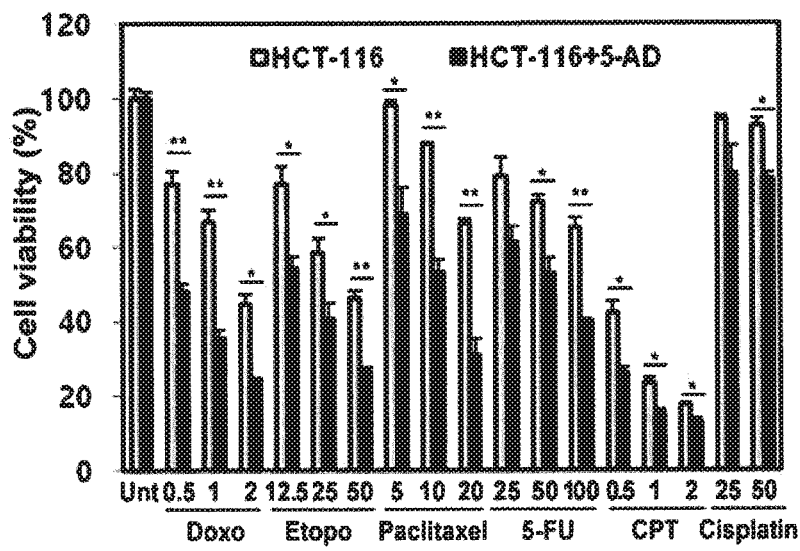
FIG. 6 shows the results of sensitizing a cancer cell line by combined treatment with a demethylating agent (5-AD) and various anticancer drugs.

When the cancer cell lines, including cervical cancer, breast cancer, colorectal cancer and bladder cancer cell lines, were treated with the anticancer chug after RIP3 expression in the cell lines was induced by 5-AD, it was observed that the cancer cell lines were sensitized to cell death. In addition to 5-AD, 5-AZA also induced RIP3 expression, and combined treatment of cancer cell lines with the demethylating agent and various anticancer drugs, such as Doxorubicin, Etoposide, Paclitaxel, 5-FU, CPT or Cisplatin, showed the effect of sensitizing the cancer cell lines to cell death (FIGS. 4 to 6).

Example 4

Figure 7:
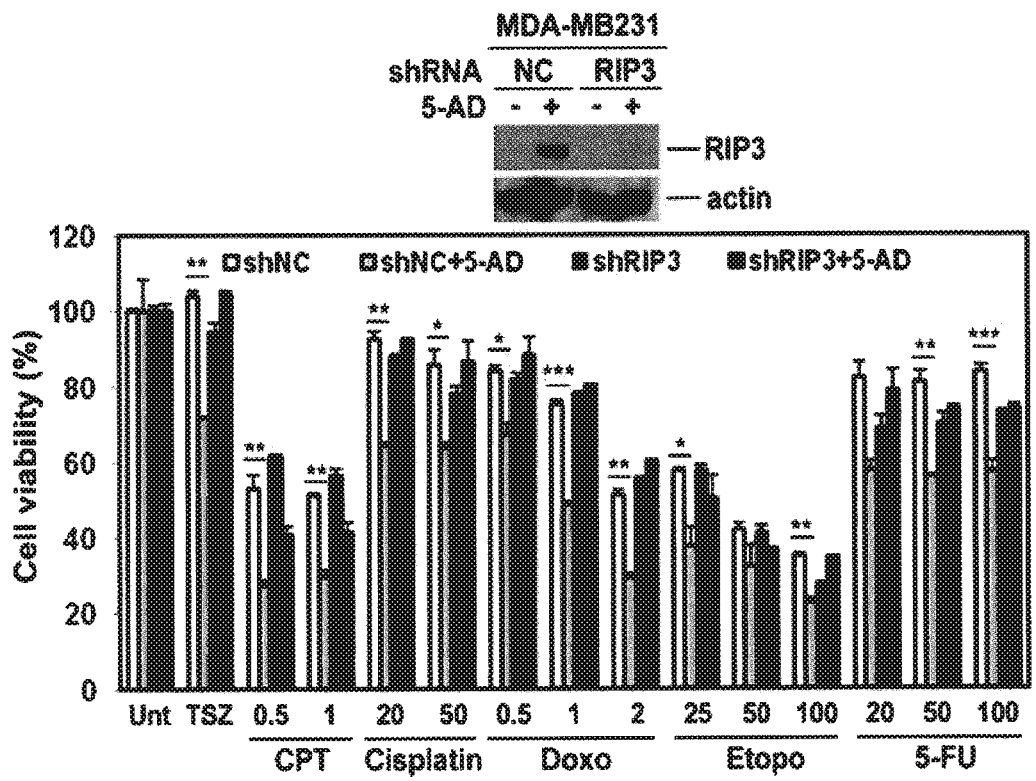
FIG. 7 shows the results of inhibiting the cancer cell death-sensitizing effect of a demethylating agent (5-AD) by RIP3 silencing.

Inhibition of Cancer Cell Death-Sensitizing Effect of Demethylating Agent by Inhibition of RIP3 Expression Since a demethylating agent (5-AD or 5-AZA) is not a drug specific for a particular protein, it may cause expression of various proteins in addition to RIP3. Thus, in order to determine whether sensitization to cell death by combined treatment with the anticancer drug and the demethylating agent is an effect induced by proteins other than RIP3, an experiment was performed using the shRIP3 cell line that specifically inhibits RIP3 expression. In the non-target cell line, when the cancer cell line was treated with 5-AD, combined treatment with the demethylating agent and the anticancer drug showed the effect of sensitizing the cancer cell line to cell death by RIP3 expression, but in the shRIP3 cell line in which RIP3 expression was specifically inhibited, RIP3 was not expressed by the shRNA system, even though the cell line was treated with 5-AD. Each of the non-target cell line and the shRIP3 cell line was primarily grown to a confluence of 10-20%, and then treated twice with 5-AD for 4 days, and whether RIP3 was expressed in the cell lines was determined. When a cell viability assay was performed based on the obtained results, it could be seen that, in the case of the shRIP3 cell line that expresses no RIP3, the sensitization effect was inhibited, suggesting that RIP3 is an important molecule in the sensitization to cell death by combined treatment with the demethylating agent and the anticancer drug. In addition, it suggests that inducing RIP3 expression is a novel anticancer strategy that may increase the death of cancer cells. After whether RIP3 was expressed was determined, a cell viability assay was performed. As a result, in the case of the shRIP3 cancer cell line, it could be seen by a Western blotting technique that RIP3 was not expressed even when the cancer cell line was treated with 5-AD, and it could be seen by a MTT technique that the sensitization to cell death by combined treatment with the demethylating agent and the anticancer drug was inhibited. On the contrary, in the case of the non-target cell line, it was shown that RIP3 expression was induced when the cancer cell line was treated with 5-AD, and that combined treatment of the cancer cell line with the demethylating agent and various anticancer drugs, such as CPT, Doxorubicin, Cisplatin, Etoposide and 5-FU, showed the effect of sensitizing the cancer cell line to cell line. Such results demonstrated that RIP3 is a key molecule in sensitization to a cancer cell (FIG. 7).

Example 5

Figure 8:
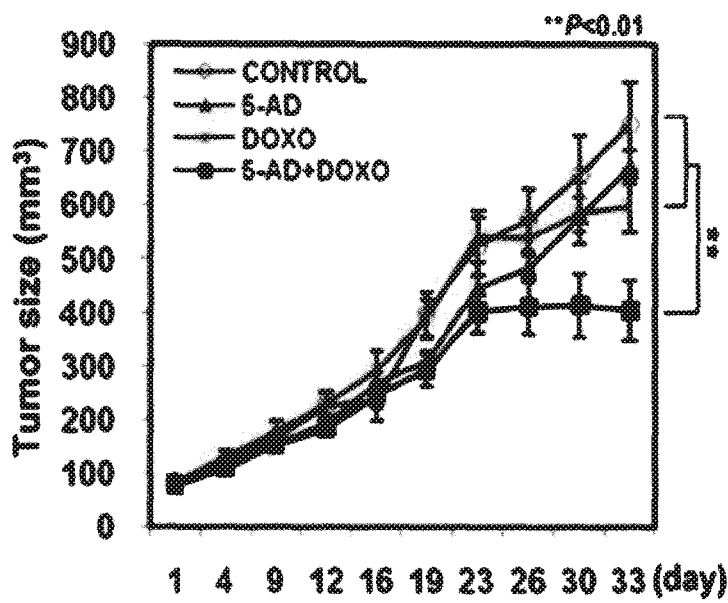
FIG. 8 shows the results obtained by injecting the MDA-MB231 breast cancer cell line into BALB/c nude mice to form tumors, and then injecting 5-AD for 1 week, injecting Doxorubicin for 33 days, and measuring a change in the volume of the tumor tissue.
Figure 9:
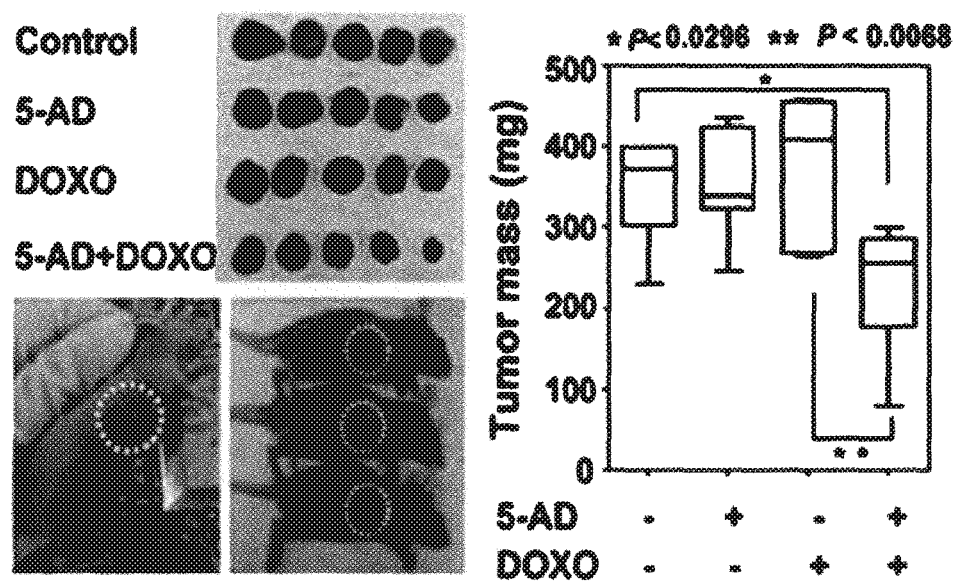
FIG. 9 shows the results of measuring the mass of the tumor isolated after the last combined treatment with 5-AD.
Figure 10:
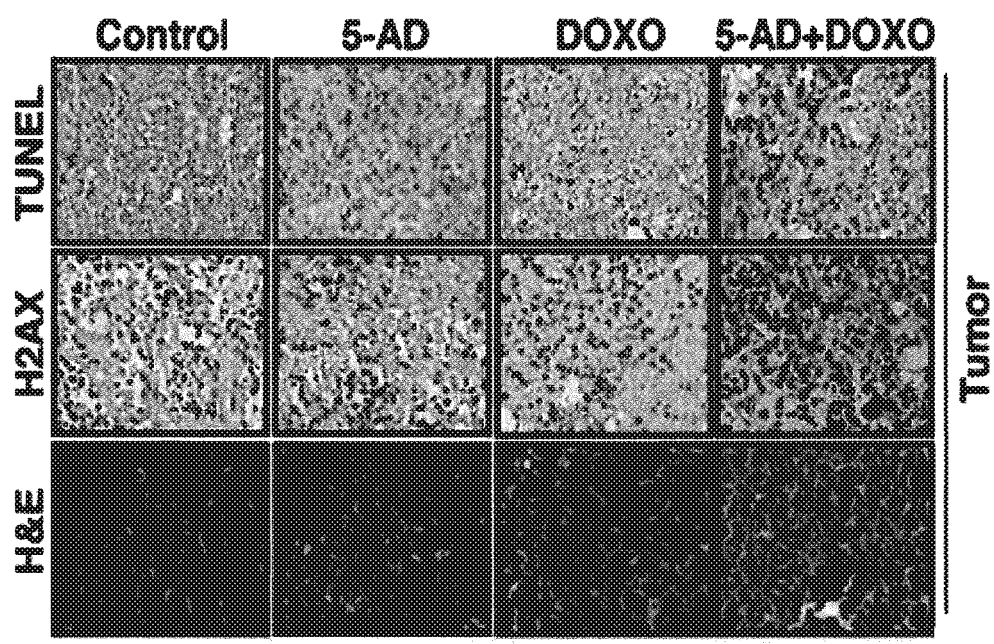
FIG. 10 shows the results of H & E staining, p-H2AX antibody staining and TUNEL staining of paraffin blocks prepared from tumor tissues subjected to combined treatment with 5-AD and Doxorubicin.

Verification of Anticancer Drug Sensitive by RIP3 Expression in Mouse Xenograft Model In order to verify the sensitization effect induced by RIP3 expression in experimental animal models, the MDA-MB231 breast cancer cell line that expresses no RIP3 was injected into BALB/c nude mice to form tumors. Next, the mice were injected with 5-AD for 1 week, and then injected with Doxorubicin for 33 days, and a change in the volume of the tumor tissue was measured. As a result, it was observed that the volume of the tumor tissue was significantly reduced by combined treatment with Doxonibicin and 5-AD compared to treatment with Doxorubicin alone (FIG. 8). In addition, the tumor tissue was isolated after the last drug treatment, and the mass thereof was measured. As a result, similar to the results of analyzing the tumor tissue present in the mice, it was observed that the mass of tumor tissue was significantly reduced by combined treatment with Doxorubicin and 5-AD (FIG. 9). The tumor tissue subjected to combined treatment with 5-AD and Doxorubicin was prepared into a paraffin block which was then visualized by H&E staining, p-H2AX antibody staining, and TUNEL staining. As a result, it was observed that the volume of the tumor tissue in the group subjected to the combined treatment was significantly reduced, suggesting that cytotoxicity to the cancer cells and the death of the cancer cells occurred by the combined treatment (FIG. 10).

Figure 11A:
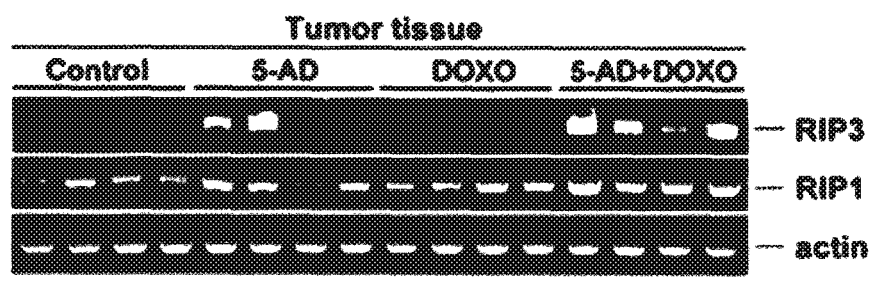
FIG. 11a shows the results of performing RT-PCR on RNA extracted from tumor tissues subjected to combined treatment with 5-AD and Doxorubicin.
Figure 11B:
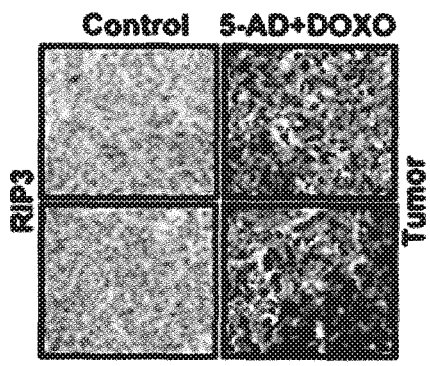
FIG. 11b shows the results of immunohistochemistry (IHC) performed to measure increased expression of RIP3 in paraffin blocks prepared from isolated tumor tissues.

In addition, RNA was extracted from the isolated tumor tissue and subjected to RT-PCR. As a result, it was shown that RIP3 expression in the group treated with 5-AD was increased. Furthermore, the isolated tumor tissue was prepared into a paraffin block which was then subjected to immunohistochemistry (IHC), and as a result, it was confirmed again that RIP3 expression was increased (FIG. 11). Such results obtained through the experiment performed at the cellular level in the experimental animal models could verify that the increased expression of RIP3 enhanced anticancer drug sensitivity.

Example 6

Immunostaining Assay of Normal Breast Tissue and Breast Cancer Tissue

In order to confirm whether RIP3 is expressed in actual cancer patients, tumor tissue and non-tumor tissue were isolated from 132 breast cancer patients and prepared into paraffin blocks. The prepared paraffin block was sectioned to a thickness of 4.5 µm, and then plated on a slide. The sections were deparaffinized in xylene and rehydrated in a graded series of ethanol-aqueous solutions, and then treated with hydrogen peroxide to eliminate non-specific enzymatic reaction, followed by treatment with citric acid solvent to dissociate latent antigen. Then, it was incubated with diluted normal serum for 20 minutes to block non-specific reaction, and then reacted with RIP3 antibody (1:300) for 24 hours. After washing with water, the resulting material was incubated with biotin-conjugated secondary antibody for 30 minutes, followed by washing with water. After it was incubated with an avidin-biotin complex for 30 minutes, and then washed with water, it was treated with a DAB color development solution for 5 minutes. Next, the nucleus was stained with hematoxylin, washed with water, and then subjected to a mounting process.

The intensity of color development by DAB was graded 0 (no color development), 1 (weak color development), 2 (moderate), or 3 (strong color development), and H-score was obtained by multiplying the proportion of stained cells and staining intensity. Staining was interpreted by an experienced pathologist.

Figure 12A:
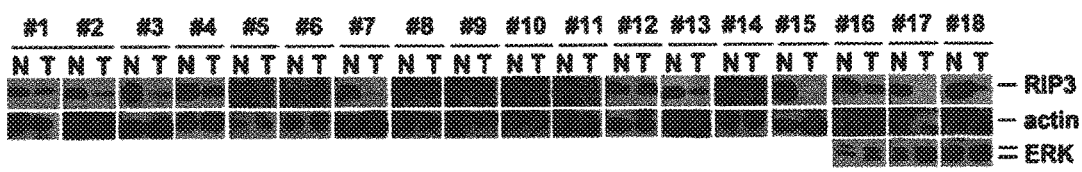
FIG. 12a shows the results of analyzing the expression of RIP3 from the protein isolated from typical normal breast tissue and breast cancer tissue.
Figure 12B:
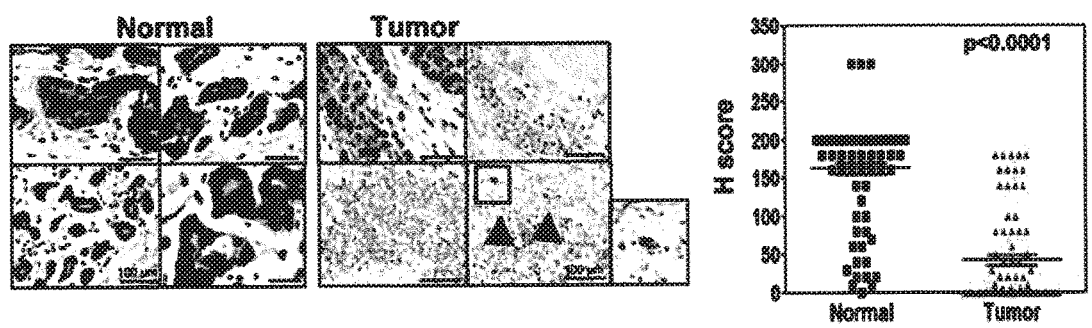
FIG. 12b shows immunostaining images of RIP3 in typical normal breast tissue and breast cancer tissue, and H-score of RIP3 immunostaining in typical normal breast tissue and breast cancer tissue.
Figures 13, 14:
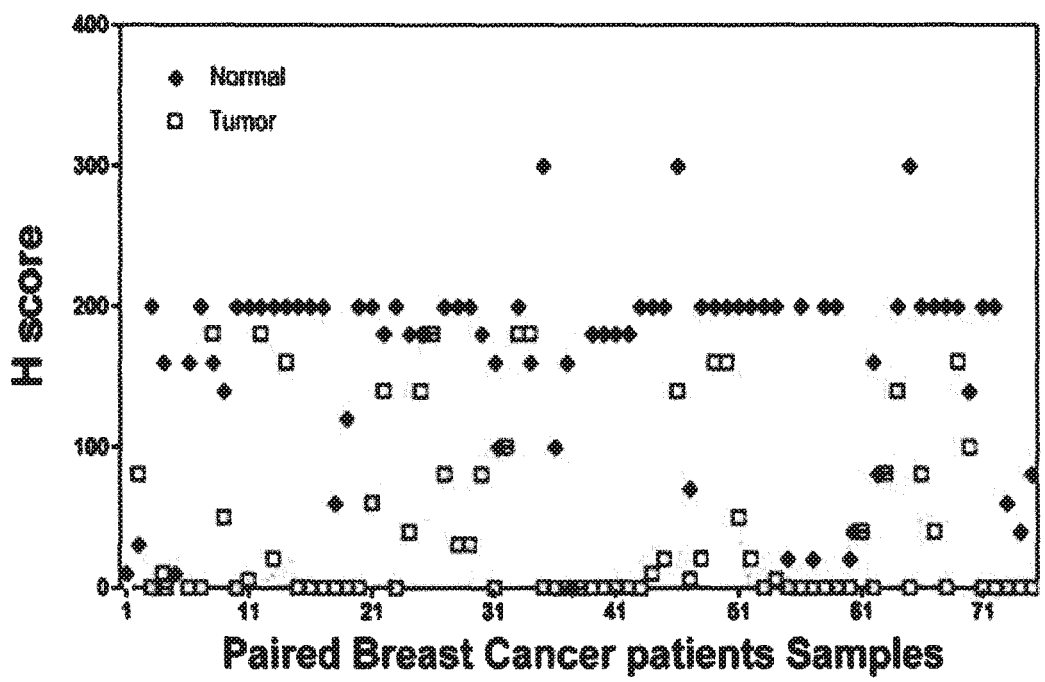
FIG. 13 shows representative H-score of RIP3 immunostaining in the normal breast tissue and breast cancer tissue obtained from the same patient.
FIG. 14 shows the viability of RIP3-silenced cells treated with various concentrations of anticancer drugs.

RIP3 in the normal breast tissue and breast cancer tissue of the same patient was analyzed by a Western blotting technique, and as a result, it could be seen that RIP3 expression in the cancer tissue was significantly reduced (FIG. 12a). In addition, RIP3 expression in typical normal breast tissue and breast cancer tissue was analyzed by an immunohistochemical technique, and the results of the analysis are shown in representative images and as H-score (FIG. 12b). As a result, RIP3 expression was significantly lower in the breast cancer tissue of each patient than in the normal breast tissue (FIG. 13).

Example 7

Viability Assay of RIP3-Silenced HT-29 Cells by Treatment with Various Concentrations of Anticancer Drug In order to identify the role of RIP3 in anticancer drug sensitivity, the HT-29 cell line which is a representative cancer cell line expressing RIP3 was used. To identity the function of RIP3, RIP3 expression was inhibited using the shRNA system and analyzed by a Western blotting technique.

In the present invention, in order to examine whether the RIP3 gene is associated with anticancer drug sensitivity, HT-29 cells transfected with RIP3 shRNA were treated with varying concentrations of doxorubicin and etoposide, and then the cell viability of the cancer cells was measured. Particularly, HT-29 cells transfected with RIP3 shRNA were treated with 2.5 µM and 5 µM of doxorubicin and 50 µM and 100 µM of etoposide, and then incubated for 48 hours. After the medium was replaced with a fresh medium containing 0.1 mg of MTT (3-([4,5-dimethylthiazol-2-yl]-2,5-diphenyltetrazolium bromide), the cells were further incubated for 2 hours. Colorimetric analysis was performed on a precipitate obtained by reducing a tetrazolium salt, in which viable cells is dissolved, into a purple formazan crystal. Next, the medium was removed, and the produced formazan crystal was dissolved in 500 µl of DMSO, and the absorbance was measured using an ELISA reader at 570 nm. Cell viability was expressed as a percentage relative to the control taken as 100% viability.

As a result, as shown in FIG. 14 (right), in the control group, the cell viability decreased depending on the concentration of doxorubicin and etoposide, whereas in the test group in which RIP3 was knocked down with shRNA, the cell viability significantly increased compared to that of the control group. Such results demonstrated that RIP3 plays a key role in anticancer drug sensitivity (FIG. 14).

Example 8

Viability Assay of RIP3-Silenced T47D Cells by Treatment with Various Concentrations of Anticancer Drug The T47D cell line which is a breast cancer cell line expressing RIP3 was used to identify the role of RIP3 in various kinds of cancel. First, the shRIP3 T47D cell line was prepared in the same manner as described in Example 7.

Figure 15:
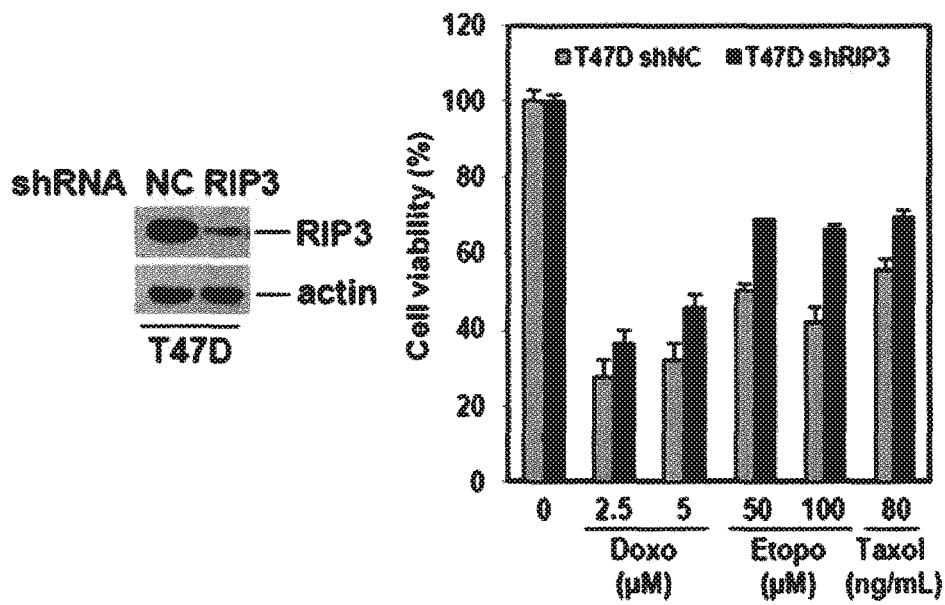
FIG. 15 shows the viability of RIP3-silenced T47D cells treated with various concentrations of anticancer drugs.

The results of Western blotting indicated that the RIP3 protein was not substantially detected in the T47D cells transfected with RIP3 shRNA and that the RIP3 gene was effectively knocked down (FIG. 15). In order to examine whether RIP3 increases anticancer drug sensitivity in T47D breast cancer cells, an MTT assay was performed. A control group and a RIP3-knocked down test group were incubated with doxorubicin, etoposide and taxol at the concentrations shown in FIG. 15 (right) for 48 hours. The results of the MTT assay indicated that the cells of the control group were killed depending on the concentration of the anticancer drugs, whereas the anticancer drug resistance of the RIP3-transfected cell line significantly increased compared to that of the control group.

From the above results, it could be found that the regulation of RIP3 expression influences the anticancer drug resistance of cancer cell lines. Particularly, it could be seen that, when RIP3 expression was inhibited, the cancer cells had resistance to the anticancer drug, and thus the activity of the anticancer drug was inhibited, whereas when RIP3 was expressed, the death of cancer cells increased depending on the concentration of the anticancer drug.

Example 9

Analysis of 10-Year Metastatic Relapse-Free Survival of Breast Cancer Patients

Figure 16:
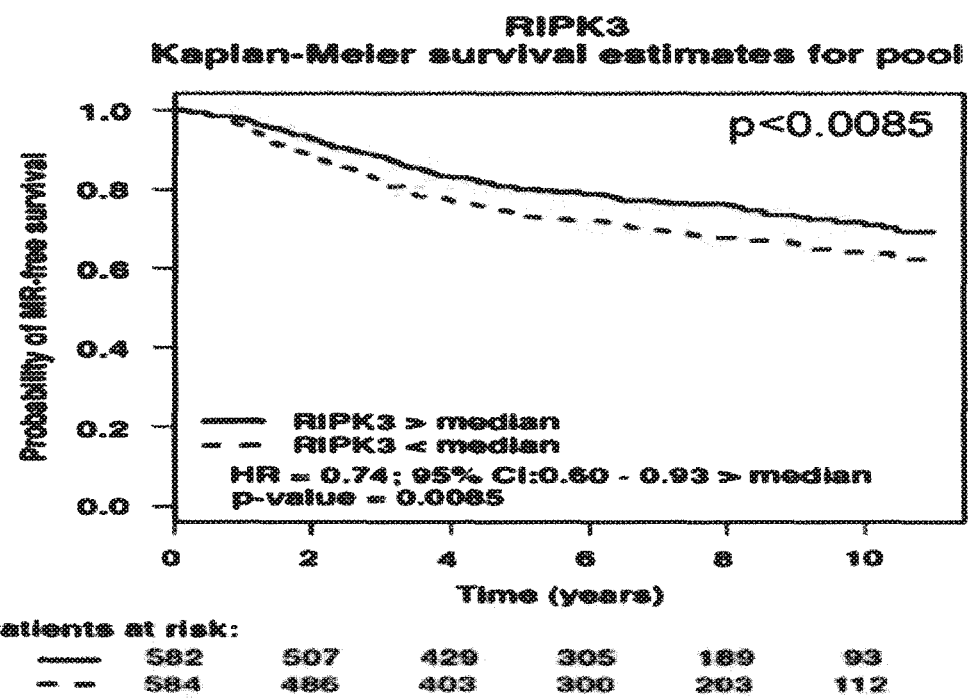
FIG. 16 is a graph showing the results of analyzing the 10-year metastatic relapse-free survival of 1,166 breast cancer patients.

FIG. 16 is a graph showing the 10-year metastatic relapse-free survival of 1,166 breast cancer patients. The expression level of the RIP3 gene was divided into two (above and below 50%), and the survival rate of the patients was analyzed. As a result, it was shown that the survival rate of the patients increased as the expression level of RIP3 increased. Such results showed a statistically significant difference ($p<0.0085$), suggesting that the expression level of RIP3 influences the survival rate of the patients. The results were analyzed using the Breast Cancer Gene-Expression Miner v3.0 software designed by Jezequel et al. (Breast Cancer Research and Treatment 2012; 131: 765-75).

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

The invention claimed is:

1. A method for enhancing an anticancer chemotherapeutic drug sensitivity in a subject in need of the anticancer drub treatment, comprising administering an effective amount of a receptor-interacting protein kinase-3 (RIP3) protein expression inducing agent to the subject, wherein the RIP3 protein expression inducing agent is a demethylating agent which is selected from 5-aza-2'-deoxycytidine (5-AD), 5-azacytidine (5-AZA) and RG108, wherein the anticancer chemotherapeutic drug is selected from Doxorubicin, Etoposide, Paclitaxel, Fluorouracil, Camptothecin and Cisplatin.

2. The method of claim 1, wherein the subject has breast cancer, cervical cancer, glioma, brain cancer, melanoma, lung cancer, bladder cancer, prostate cancer, leukemia, renal cancer, liver cancer, colorectal cancer, pancreatic cancer, gastric cancer, gallbladder cancer, ovarian cancer, lymphoma, osteosarcoma, uterine cancer, oral cancer, bronchial cancer, nasopharyngeal cancer, larynx cancer, skin cancer, blood cancer, thyroid cancer, parathyroid cancer, or ureter cancer.

3. The method of claim 1, further comprising administering the anticancer chemotherapeutic drug to the subject.

* * * * *